(12) United States Patent
Stahlhut et al.

(10) Patent No.: US 7,983,788 B2
(45) Date of Patent: *Jul. 19, 2011

(54) METHOD FOR ANALYZING REFLECTION PROPERTIES

(75) Inventors: Oliver Stahlhut, Wedemark/OT Mellendorf (DE); Christian Neumann, Hildesheim (DE); Michael Mäker, Hannover (DE)

(73) Assignee: Benecke-Kaliko AG, Hannover (DE)

( * ) Notice: Subject to any disclaimer, the term of this patent is extended or adjusted under 35 U.S.C. 154(b) by 212 days.

This patent is subject to a terminal disclaimer.

(21) Appl. No.: 12/339,918

(22) Filed: Dec. 19, 2008

(65) Prior Publication Data

US 2009/0157210 A1 Jun. 18, 2009

Related U.S. Application Data

(63) Continuation of application No. PCT/EP2007/053967, filed on Apr. 24, 2007.

(30) Foreign Application Priority Data

Jun. 20, 2006 (DE) .......................... 10 2006 028 238

(51) Int. Cl.
| | |
|---|---|
| G06F 19/00 | (2006.01) |
| G06T 17/00 | (2006.01) |
| G06T 15/30 | (2006.01) |
| G06T 17/20 | (2006.01) |
| G09G 5/00 | (2006.01) |
| G09G 5/02 | (2006.01) |
| G01C 3/08 | (2006.01) |
| G01N 21/00 | (2006.01) |
| G01B 11/30 | (2006.01) |
| G01B 11/24 | (2006.01) |
| G06K 9/00 | (2006.01) |
| G06K 9/40 | (2006.01) |

(52) U.S. Cl. ........ 700/163; 700/118; 345/420; 345/423; 345/583; 345/589; 356/4.07; 356/237.2; 356/600; 356/601; 382/108; 382/274

(58) Field of Classification Search .................... 700/97, 700/98, 118, 159, 160, 163; 702/33, 85, 702/97, 155, 166, 167; 345/418–423, 581–583, 345/589; 356/4.07, 237.1, 237.2, 237.5, 356/600, 601, 611; 382/108, 141, 152, 154, 382/254, 274, 276, 302
See application file for complete search history.

(56) References Cited

U.S. PATENT DOCUMENTS

| | | | | |
|---|---|---|---|---|
| 4,802,759 A | | 2/1989 | Matsumoto et al. | |
| 4,943,938 A | * | 7/1990 | Aoshima et al. | 345/422 |
| 4,973,154 A | * | 11/1990 | McMichael et al. | 356/5.09 |
| 4,986,664 A | | 1/1991 | Lovoi | |
| 5,003,615 A | * | 3/1991 | Seitz | 382/108 |
| 5,281,798 A | | 1/1994 | Hamm et al. | |
| 5,406,342 A | * | 4/1995 | Jongsma | 351/212 |
| 5,488,477 A | * | 1/1996 | de Groot | 356/514 |
| 5,864,394 A | * | 1/1999 | Jordan et al. | 356/237.2 |
| 5,953,578 A | * | 9/1999 | Lee | 438/9 |
| 6,345,195 B1 | * | 2/2002 | Herskowits et al. | 600/473 |
| 6,555,836 B1 | * | 4/2003 | Takahashi et al. | 250/559.19 |
| 6,700,563 B1 | * | 3/2004 | Koizumi | 345/156 |
| 6,700,840 B2 | * | 3/2004 | Clark | 369/44.23 |
| 6,714,892 B2 | * | 3/2004 | Houge et al. | 702/155 |
| 6,762,839 B2 | * | 7/2004 | Zeylikovich et al. | 356/397 |
| 6,850,242 B1 | * | 2/2005 | Saito | 345/582 |
| 6,888,544 B2 | * | 5/2005 | Malzbender et al. | 345/423 |
| 7,139,078 B2 | * | 11/2006 | Hogan | 356/480 |
| 7,330,273 B2 | * | 2/2008 | Podoleanu et al. | 356/497 |
| 7,333,175 B2 | * | 2/2008 | Baselmans | 355/55 |
| 7,363,180 B2 | * | 4/2008 | Swaringen et al. | 702/85 |
| 7,446,880 B2 | * | 11/2008 | Vollmer et al. | 356/480 |
| 7,616,323 B2 | * | 11/2009 | De Lega et al. | 356/511 |
| 7,822,294 B2 | * | 10/2010 | Ohlinger et al. | 382/302 |
| 2005/0146722 A1 | | 7/2005 | Torfs et al. | |
| 2006/0278613 A1 | * | 12/2006 | Hess | 216/83 |
| 2008/0137101 A1 | * | 6/2008 | Spence et al. | 356/611 |
| 2009/0157215 A1 | * | 6/2009 | Stahlhut et al. | 700/118 |
| 2009/0196477 A1 | * | 8/2009 | Cense et al. | 382/131 |

FOREIGN PATENT DOCUMENTS

| | | | |
|---|---|---|---|
| JP | 02298095 A | * | 12/1990 |
| WO | 9312905 A1 | | 7/1993 |
| WO | WO 2007147664 A1 | * | 12/2007 |
| WO | WO 2007147674 A2 | * | 12/2007 |

OTHER PUBLICATIONS

International Search Report dated Aug. 30, 2007.

* cited by examiner

Primary Examiner — Crystal J Barnes-Bullock
(74) Attorney, Agent, or Firm — Laurence A. Greenberg; Werner H. Stemer; Ralph E. Locher

(57) ABSTRACT

A method allows analyzing and describing the reflective properties of a three-dimensionally structured original surface. The topology of the original surface is determined and the topological data are stored in the form of a depth map in a first data record and evaluated with respect to the influence of the data on the reflective properties. Each surface element is assigned a reflective value in accordance with the evaluation and the value is stored in a second data record and made available to other machining or inspection systems. There, the reflection values of the second data record are divided into classes and the depth values of the first data record, assigned to the classified reflection values, are varied in accordance with the classification. Finally, the changed depth values are employed as parameters for electronically controlling a tool in order to machine the artificially produced surface.

7 Claims, No Drawings

METHOD FOR ANALYZING REFLECTION PROPERTIES

CROSS-REFERENCE TO RELATED APPLICATIONS

This is a continuation, under 35 U.S.C. §120, of copending international patent application PCT/EP2007/053967, filed Apr. 24, 2007, which designated the United States; this application also claims the priority, under 35 U.S.C. §119, of German patent application DE 10 2006 028 238.8, filed Jun. 20, 2006; the prior applications are herewith incorporated by reference in their entirety.

BACKGROUND OF THE INVENTION

Field of the Invention

The invention relates to a method for analyzing and describing the reflection properties of a three-dimensionally structured original surface, in particular an embossed surface, in the form of a data record that is made available to a machining system or testing system for surfaces.

Methods for assessing and/or analyzing the reflection behavior of surfaces are known.

One of the simplest methods consists, for example, in determining a "degree of gloss" according to standardized measurement conditions, for example ISO 2813. There, the optical radiation reflected at an angle of 60° from the surface is measured and is assigned to a classification in degrees of gloss from matt to glossy, depending on percentage reflection. However, such a degree of gloss describes merely the averaged glossability of the entire surface considered for a specific light ratio.

Moreover, methods exist in which a statement regarding the substance itself is obtained by analyzing the reflection behavior of its surface. This is used, for example, when analyzing material samples such as liquids or powders, when examining welded joints or, for example, when controlling machining processes. Thus, for example, U.S. Pat. No. 5,281,798 and international PCT application WO 93/12905 describe a method for removing surface coatings/paints on a substrate, the method being controlled by the evaluation of a color difference of a reflected light such that only the coating to be eroded is removed, and the substrate itself is not damaged.

Concerning the production of artificial surface structures or surface coatings such as, for example, when producing artificial leather or plastic molded skins for parts of the inner cladding of motor vehicles, that is to say, for example, of door claddings or dashboards, methods are known in which the reflection properties of a reference surface/patterned surface are evaluated under controlled illumination and used as a basis for further control or working processes. It is peculiar to most of these methods of determination that the subjective evaluation of a practiced observer has so far been exclusively decisive between strongly or weakly reflecting subregions of a reference surface. Such a subjective evaluation can, however, disadvantageously only be transferred with insufficient accuracy into image processing or into automatic systems influencing the production process.

On the other hand, the subjective evaluation by the human eye is an extremely precise type of assessment of a structured surface that itself clearly registers even very small variations in the appearance of the surface, and has so far not proved to be replaceable by automatic methods. Transitions or boundary regions that arise, for example, owing to the juxtaposition of subsegments to form a total surface, the formation of repeats and moulette streaks are rendered just as visible as different or "unnaturally" acting optical reflection and/or optical refraction that results, for example from a chessboard-type patterning in the surface.

If, for example, it is wished to produce a plastic molded skin with a leather grain acting as naturally as possible, the reflection behavior, in particular, plays a large role. When looking at a leather surface, the human eye is accustomed to a specific reflection behavior in the case of different light ratios, and reacts extremely dismissively to artificial leather surfaces which precisely lack just this reflection behavior. A dashboard that is covered with a plastic molded skin with a leather grain that unpleasantly reflects in sunlight is rejected by the consumer. This frequently leads to the fact that when such molded skins are produced an additional three-dimensional "artificial" structure that diminishes the reflection is impressed, for example in the form of a regular perforation. However, as a general rule the impression of a "genuine leather surface" is thereafter no longer present.

SUMMARY OF THE INVENTION

It is accordingly an object of the invention to provide a method for analyzing reflection properties which overcomes the above-mentioned disadvantages of the heretofore-known devices and methods of this general type and which allows determining the reflection properties of a surface objectively, which moreover converts the reflection properties into parameters that can be made available to downstream systems, and which permits a description of the reflection properties in a manner that is true to nature and makes these properties available in the form of a data record, inter alia for the production of artificial surfaces.

DETAILED DESCRIPTION OF THE INVENTION

With the foregoing and other objects in view there is provided, in accordance with the invention, a method of analyzing and describing reflection properties of a three-dimensionally structured original surface, such as an embossed surface. The method according to the invention comprises:

a) firstly the topology of the original surface is determined with the aid of a three-dimensional scanning method, and the topological data thus determined and essentially comprising the heights and depths belonging to each surface element of a screen (i.e., raster) spanning the original surface, are stored in a first data record, each surface element or raster element being assigned a measured depth value such that a depth map of the original surface results;

b) the first data record is subjected to an assessment of the depth values with regard to their influence on the reflection properties;

c) a reflection value is assigned to each surface element, depending on the assessment, and is stored in a second data record;

whereupon the second data record containing the reflection values/parameters assigned to each surface element is made available to a further machining system or testing system.

While the prior art methods include only a subjective evaluation of the total surface via the degree of gloss or, under the influence of virtual illumination sources, allocate a reflection in a generalized way to a surface via photos or CAD (Computer Aided Design) simulation, the important novel step in the case of the inventive solution consists in the coupling of the reflection properties of a surface to the macroscopic depth structure, actually present in the three-dimensional surface, in differentially small surface elements. The inventive method thus departs from a generalized approach, and generates a correlation of depth structure, that is to say the highly resolved topological map of the surface, and the local reflection behavior.

In accordance with a preferred development the steps b) and c) are configured and designed such that:

b) the first data record is subjected to an edge detection and subsequently an averaging with reference to the depth values, and c) the value that is obtained by the averaging and describing the frequency and/or height of the edges is assigned to each surface element as reflection value and is stored in a second data record.

Proceeding from the physical effect of the scattering of the light at edges, and from the reflectivity influenced thereby, of a randomly arranged number of edges, the solution formed further here consists in rendering the method, known per se from image processing, of edge detection by means of specific mathematical operators, that is to say, for example, by means of Sobel or Laplace operators, useful for reflection analysis of three-dimensional surfaces by for the first time providing as data for the calculation actual and physically present depth information and/or depth differences, that is to say actual edges.

Specifically, in image processing to date all that has been performed is a two-dimensional viewing, detection and processing of "boundaries" within an image that have been formed by brightness differences. These boundaries are denoted as "edges" and their detection as "edge detection". Such an edge detection is used, for example, to detect or count on an assembly line objects that are to be machined and are photographed or filmed with the aid of a camera. Such a two-dimensional viewing is certainly sufficient for detecting two-dimensional spatial assignments, but not sufficient for the complicated structure of a three-dimensional surface, nor for the modeling of a reflection property to be derived therefrom.

The reflection properties described by the reflection values need not, incidentally, be stored as absolute values; relative reflection values, that is to say the differences between the reflection values of individual surface elements, suffice for carrying out the method, and also for use thereof. For example, relative frequencies of edges can be stored as a parameter that describes the reflection value.

One development consists in that the averaging is performed after the edge detection such that surface elements are combined into groups, and in each case edge frequencies and/or heights averaged inside the groups by proximity operations are assigned to the groups and stored in the second data record. For example, such an averaging is performed by a Gaussian filter as operator. This yields a characterization or generalization by means of which the, if appropriate, greatly varying number and thickness/height of the edges are ascribed to appropriately homogenized reflection values that can be advantageous in the further method and, for example, in the use of data to control processing machines.

One further advantageous development consists in that a directionally dependent filtering of the depth values of the first data record is performed before the edge detection. By means of such a directionally dependent filtering that can be carried out with the aid of various mathematical operators, the statement regarding the reflectivity, which is oriented only toward edge height and edge frequency by the normal edge detection, is substantially refined such that the reflection properties can likewise be represented objectively and measurably for different illumination conditions or angles of view.

A further advantageous development consists in that the filtering is performed before the edge detection by a directed Gaussian filtering. What is involved here is a simple operator that works rapidly and enables a sufficient number of directions to be represented with regard to their reflection properties within acceptable times.

One advantageous development consists in that the so-called ray tracing method is used to determine the reflection properties/reflection values of actual three-dimensional structures by designing the method steps b) and c) such that b) an optical radiation acting on the contour, characterized by the first data record of the depth values, of the original surface is described by a simulation model, and that c) the reflection of said optical radiation is calculated from the depth discontinuities of the irradiated surface elements, assigned to a reflection value and stored in a second data record.

On the basis of the strictly physical alignment—and depending on simulation model—this development of the method returns very good results in the objective description of the reflectivity, but necessitates a substantial outlay on computation, particularly in the case of the directionally dependent viewing.

With the above and other objects in view there is also provided, in accordance with the invention, a method for influencing/improving the reflection properties of artificially produced surfaces, in particular surfaces of embossed plastic films. The above-outlined method is thus continued as follows:

d) the reflection values of the second data record are divided into classes;

e) the depth values, assigned to the classified reflection values, of the first data record are varied in accordance with the classification; and f) the varied depth values are used as parameters for electronically controlling a tool in order to machine the artificially produced surface.

The inventive method can thus be used for any type of method for producing artificial surfaces. The depth structures of a surface that are modified and thus optimized with regard to the reflection property can therefore be superposed as simple parameters on any basic depth scheme/structure scheme howsoever produced in advance, and are therefore directly available as controlled variables. By way of example, such a use would enable a leather selected for an automobile interior on the basis of its shape and embossment, for example water buffalo leather, which although possessing a "robust impression" desired by the consumer, reflects unpleasantly on a dashboard given a specific incidence of light to be produced as a plastic molded skin with a reflection optimized depth structure, without influencing the overall impression desired.

The invention claimed is:

1. A method of influencing reflection properties of a three-dimensionally structured original surface, which comprises:

a) firstly determining a topology of the original surface with the aid of a three-dimensional scanning method, to thereby establish topological data primarily including height values and depth values belonging to each surface element of a raster spanning the original surface, storing the topological data in a first data record, and assigning each surface element a measured depth value to form a depth map of the original surface;

b) subjecting the first data record to an assessment of the depth values with regard to an influence thereof on the reflection properties;

c) assigning a reflection value to each surface element, depending on the assessment, and storing the reflection values in a second data record;

subsequently controlling a tool in a machining system on the basis of the second data record containing the reflection values assigned to each surface element and machining selected surface elements to influence the reflection properties thereof.

2. The method according to claim 1, wherein:

step b) further comprises subjecting the first data record to an edge detection and subsequently to an averaging with reference to the depth values; and step c) further comprises assigning to each surface element a value that is obtained by the averaging and that describes a frequency and/or a height of the edges as a reflection value and storing the reflection value in a second data record.

3. The method according to claim 2, which comprises averaging after the edge detection such that surface elements are combined into groups, and assigning in each case edge frequencies and/or heights averaged inside the groups by proximity operations to the groups and storing same in the second data record.

4. The method according to claim 2, which further comprises performing a directionally dependent filtering of the depth values of the first data record prior to the edge detection.

5. The method according to claim 4, wherein the filtering comprises directed Gaussian filtering.

6. The method according to claim 1, wherein:

step b) comprises describing with a simulation model an optical radiation acting on the contour of the original surface characterized by the first data record of the depth values; and step c) comprises calculating the reflection of the optical radiation in dependence on the depth discontinuities of the irradiated surface elements, assigning same to a reflection value, and storing same in a second data record.

7. A method of influencing/improving reflection properties of a surface of an embossed plastic film, which comprises:

a) firstly determining a topology of the surface with a three-dimensional scanning method, to thereby establish topological data primarily including height values and depth values belonging to each surface element of a raster spanning the original surface, storing the topological data in a first data record, and assigning each surface element a measured depth value to form a depth map of the original surface;

b) assessing the depth values of the first data record with regard to an influence thereof on the reflection properties;

c) assigning a reflection value to each surface element based on the assessing step, and storing the reflection values in a second data record;

d) dividing the reflection values of the second data record into classes;

e) changing the depth values of the first data record, assigned to the classified reflection values, in accordance with the classification; and f) using the changed depth values as parameters for electronically controlling a tool and machining the embossed plastic film with the tool under guidance of the parameters defined by the changed depth values.

* * * * *